(12) United States Patent
Nakel

(10) Patent No.: US 12,702,744 B2
(45) Date of Patent: Aug. 11, 2026

(54) WORKING FLUID TREATMENT DEVICE FOR MASS TRANSFER BETWEEN A WORKING FLUID AND TWO FLUID EXCHANGE MEDIA

(71) Applicant: Maquet Cardiopulmonary GmbH, Rastatt (DE)

(72) Inventor: Mathias Nakel, Burladingen/Ringingen (DE)

(73) Assignee: Maquet Cardiopulmonary GmbH, Rastatt (DE)

( * ) Notice: Subject to any disclaimer, the term of this patent is extended or adjusted under 35 U.S.C. 154(b) by 0 days.

(21) Appl. No.: 17/077,752

(22) Filed: Oct. 22, 2020

(65) Prior Publication Data

US 2021/0121620 A1 Apr. 29, 2021

Related U.S. Application Data

(60) Provisional application No. 62/926,210, filed on Oct. 25, 2019.

(51) Int. Cl.
*A61M 1/36* (2006.01)
*A61M 1/16* (2006.01)

(52) U.S. Cl.
CPC ........ *A61M 1/3666* (2013.01); *A61M 1/1629* (2014.02); *A61M 1/3623* (2022.05)

(58) Field of Classification Search
CPC .......................... A61M 1/3666; A61M 1/1629
See application file for complete search history.

(56) References Cited

U.S. PATENT DOCUMENTS 4,151,088 A * 4/1979 Wolf, Jr. .............. B01D 63/087 210/321.75
5,162,101 A 11/1992 Cosentino et al.
(Continued)

FOREIGN PATENT DOCUMENTS

DE 102009008601 A1 * 8/2010 .............. A61M 1/16
EP 0613716 A2 7/1994
(Continued)

OTHER PUBLICATIONS

ISR/WO issued in PCT/EP2020/079692 on Apr. 15, 2021.
International Preliminary Report on Patentability and Written Opinion, issued in PCT/EP2020/079692 on Apr. 26, 2022, 13 pages.

*Primary Examiner* — Rebecca E Eisenberg
*Assistant Examiner* — Kate Elizabeth Strachan
(74) *Attorney, Agent, or Firm* — EIP US LLP

(57) ABSTRACT

An extracorporeal blood treatment device comprises a single housing defining an internal blood flow cavity. The housing accommodates an oxygenator, a heat exchanger and an additional mass transfer assembly, each having an array of fluid conduits. The arrays are co-located within the internal blood flow cavity such that blood flowing through the internal blood flow cavity flows substantially homogeneously around all the conduits. The arrays are arranged relative to one another within the internal blood flow cavity such that they together define a continuous blood flow path through the internal blood flow cavity along which blood can flow. The continuous blood flow path has a blood entry surface at one end and a blood exit surface at the opposite end. The overall blood flow direction from the blood entry surface along the blood flow path to the blood exit surface follows substantially a straight line.

27 Claims, 8 Drawing Sheets

(56) References Cited

U.S. PATENT DOCUMENTS

| | | | | |
|---|---|---|---|---|
| 10,401,876 | B1 * | 9/2019 | Coleman | G05D 7/00 |
| 2012/0190103 | A1 * | 7/2012 | Maurer | A61M 1/1698 435/283.1 |
| 2015/0174311 | A1 * | 6/2015 | McLevish | B21D 53/027 422/46 |
| 2015/0246169 | A1 * | 9/2015 | Humes | A61K 31/00 435/375 |
| 2018/0236158 | A9 | 8/2018 | Haag et al. | |
| 2019/0099542 | A1 * | 4/2019 | Kuzelka | A61M 16/18 |
| 2021/0113755 | A1 * | 4/2021 | Bowers | A61M 1/1698 |

FOREIGN PATENT DOCUMENTS

| | | | |
|---|---|---|---|
| JP | H3-47268 | A | 2/1991 |
| JP | 2001-79083 | A | 3/2001 |
| JP | 2012-524626 | A | 10/2012 |
| JP | 2019-529045 | A | 10/2019 |
| WO | 2010124087 | A1 | 10/2010 |
| WO | 2018057892 | A1 | 3/2018 |
| WO | 2019166823 | A1 | 6/2019 |

* cited by examiner

WORKING FLUID TREATMENT DEVICE FOR MASS TRANSFER BETWEEN A WORKING FLUID AND TWO FLUID EXCHANGE MEDIA

This application claims priority to, and the benefit of, U.S. Provisional Application No. 62/926,210, filed Oct. 25, 2019. The disclosure of this provisional application is hereby incorporated by reference in its entirety.

FIELD OF THE DISCLOSURE

The present disclosure generally relates to working fluid treatment devices. Such devices are used to modify the properties of a working fluid, e.g., by adding substances to or removing substances from the working fluid, or by heating or cooling the working fluid.

The present disclosure more specifically relates to extracorporeal blood treatment devices, which are configured to exchange mass and/or energy between blood and fluid transport media flowing through the extracorporeal blood treatment device. In particular, the disclosure relates to extracorporeal blood treatment devices comprising an oxygenator and a heat exchanger.

BACKGROUND OF THE DISCLOSURE

Devices for treating working fluids, such as beverages, industrial gases, liquid fossil fuels or bodily fluids and, in particular blood, take many forms. A typical example is the so-called blood oxygenator.

Oxygenators are extracorporeal gas exchange devices, which enrich blood with oxygen. They may be used during surgical operations, where the blood supply from the heart to the bodily organs is interrupted. Non-limiting examples of procedures in which an oxygenator may be employed include cardiopulmonary bypass procedures, extracorporeal membrane oxygenation (ECMO) procedures, and pump assisted lung protection (PALP) procedures.

In general, oxygenators can be divided into two main groups, the so-called "bubble oxygenators" and "membrane oxygenators". The use of bubble oxygenators has considerably decreased over time because they tend to damage blood cells and plasma proteins.

Membrane oxygenators direct a blood stream into contact with a surface of a semipermeable membrane, through which $CO_2$ and $O_2$ can diffuse or be transferred. They are commonly applied to imitate the function of the lungs in a short-term cardiopulmonary bypass (CPB) and/or to oxygenate blood in a long time life support, termed extracorporeal membrane oxygenation (ECMO).

Most of the currently available CPB and ECMO systems involve various external components and accessories, including, e.g., heat exchangers, blood concentrators, bubble detectors, infusion and sample units as well as pumps, which, depending on the operational setup and patient's needs, are connected to tubing circuits of the oxygenator.

These CPB systems and ECMO systems have the disadvantage that they include a wide number of disparate components and involve a lot of tubing.

This disadvantage is less salient with commercially available membrane oxygenators comprising an integral heat exchange device. One example of such an apparatus is disclosed in WO 90/04419. This document shows an integrated blood heating and oxygenating device for use in heart surgery, which includes a central thermally conductive core positioned in an external housing. The heat exchange core has an external surface that is formed with a plurality of adjacently located blood receiving channels. The device further includes a gas permeable membrane in the form of a porous hollow fiber membrane that is fitted about the heat exchange core to cover the blood receiving channels. This membrane allows for exchange of $CO_2$ and $O_2$.

Document US 2016/0000989 A1, which is incorporated herein by reference for all it discloses, describes a carbon dioxide removal system, which is configured in a similar way to an oxygenator but is not necessarily intended to actively oxygenate the patient's blood. The system includes two chambers, each housing a hollow fiber gas exchange mat.

Document U.S. Pat. No. 8,133,195 B2 shows another extracorporeal blood treatment apparatus including an oxygenator, a heat exchanger and a blood filter. Document U.S. Pat. No. 8,133,195 B2 is incorporated herein by reference for all it discloses.

Another type of an extracorporeal blood treatment apparatus is disclosed in DE 37 33 542 A1. FIG. 10 of this document shows a device for heat and mass exchange with a modular construction, in which a heat exchanger module is joined together with an oxygenator module to form a single entity. The device may be complemented by one or more further modules, such as, e.g., a hemoconcentrator.

A disadvantage of this apparatus is the serial arrangement of the blood treatment units (heat exchanger, oxygenator, hemoconcentrator) in separate modules, which are connected to each other by means of intermediate connection rings. This results in narrowing and widening of the blood pathway, which is associated with corresponding pressure changes along the device, high shear stress and blood cell damage. When transiting from one module to the other, blood exits the hollow fibers of the first module, enters a transition chamber and then flows into the hollow fibers of the second module. The associated widening of the flow cross-section from the first fibers to the transition chamber, and the subsequent narrowing of the flow cross-section from the transition chamber to the second fibers leads to unwanted stress on the blood's components, which may damage these blood components.

Document WO 2019/166823 A1 pertains to an oxygenator with a supply gas distribution arrangement.

Document JP 2001-079083 A2 describes an artificial lung device having an oxygen adding region and a nitrogen monoxide adding region.

Document WO 2019/035869 A1 relates to a dual chamber gas exchanger.

SUMMARY OF THE DISCLOSURE

In light of the aforementioned, it is one object of the present disclosure to provide a working fluid treatment device with a high degree of integration.

It is a further object of the present disclosure to provide a particularly compact working fluid treatment device.

It is a further object of the present disclosure to provide a versatile working fluid treatment device, which allows different and multiple treatments of the working fluid, depending on the desired application.

It is a further object of the present disclosure to provide a working fluid treatment device permitting mass exchange between the working fluid and multiple different fluid exchange media.

It is a further object of the present disclosure to provide a compact extracorporeal blood treatment device comprising a membrane oxygenator integrated with a heat exchanger as well as at least one additional blood treatment assembly capable of mass exchange, with gentler blood circulation and lower pressure drop, which substantially mitigates blood cell damage.

According to one aspect of the present disclosure, there is provided a working fluid treatment device for mass transfer between a working fluid and a first fluid exchange medium, and for mass transfer between the same working fluid and a second fluid exchange medium different from the first fluid exchange medium, wherein the working fluid treatment device comprises:

- a collective first fluid exchange medium inlet that admits the first fluid exchange medium into the working fluid treatment device;
- a collective second fluid exchange medium inlet that is fluidly separate from the first fluid exchange medium inlet, and that admits the second fluid exchange medium into the working fluid treatment device; and
- an integrated working fluid treatment chamber, wherein the chamber includes
  - a working fluid inlet;
  - a working fluid outlet;
  - a first conduit group of first mass transfer conduits disposed between the working fluid inlet and the working fluid outlet, the first conduit group having
    - an entry end that receives the first fluid exchange medium into the first conduit group; and
    - an exit end that discharges spent first fluid exchange medium from the first conduit group,
  - wherein the first conduit group performs mass transfer of a first substance with the working fluid when the first fluid exchange medium flows through the first conduit group; and
  - a second conduit group of second mass transfer conduits disposed between the working fluid inlet and the working fluid outlet, the second conduit group having
  - an entry end that receives the second fluid exchange medium into the second conduit group; and
  - an exit end for discharging spent second fluid exchange medium from the second conduit group,
  - wherein the second conduit group performs mass transfer of a second substance with the working fluid when the second fluid exchange medium flows through the second conduit group;

wherein

- the first fluid exchange medium inlet is connected to the entry end of the first conduit group in order to collectively convey the first fluid exchange medium into all of the first mass transfer conduits of the first conduit group;
- the second fluid exchange medium inlet is connected to the entry end of the second conduit group in order to collectively convey the second fluid exchange medium into all of the second mass transfer conduits of the second conduit group;
- the first conduit group and the second conduit group are arranged in the chamber in-between the working fluid inlet and the working fluid outlet so that the working fluid, when travelling from the working fluid inlet into the chamber and then through the chamber and then out of the chamber via the working fluid outlet, flows around the first conduit group of first mass transfer conduits and the second conduit group of second mass transfer conduits; and
- there is an essentially homogeneous conduit distribution throughout the entire volume of the chamber so that the working fluid flow cross section remains substantially constant throughout the chamber.

Thanks to the constant flow cross-section throughout the working fluid treatment chamber, the working fluid circulates through the device in a very smooth way. Furthermore, since all the conduit groups are co-located within the same single working fluid treatment chamber, the device of the present disclosure is very compact.

In one embodiment, the first mass transfer conduits and the second mass transfer conduits may be hollow semipermeable membrane fibers.

In one embodiment, the semipermeable membranes making up the semipermeable membrane fibers may be liquid impermeable and either

- traversing-pore membranes traversed by open micropores for increased mass transfer across the membranes; or
- diffusion membranes comprising a nonporous layer preventing long-term membrane wetting.

In one embodiment, the semipermeable membranes making up the first mass transfer conduits may be traversing-pore membranes, and the semipermeable membranes making up the second mass transfer conduits may be diffusion membranes.

In one embodiment, the working fluid treatment device may further comprise a single shared fluid exchange medium outlet connected to the exit ends of the first and second conduit groups in order to receive the spent first and second fluid exchange media.

In one embodiment, the working fluid treatment device may further comprise a first fluid exchange medium outlet connected to the exit end of the first conduit group that receives the spent first fluid exchange medium, and a second fluid exchange medium outlet connected to the exit end of the second conduit group that receives the spent second fluid exchange medium, wherein the second fluid exchange medium outlet may be fluidly separate from the first fluid exchange medium outlet.

In one embodiment, the working fluid, when travelling through the device, may sequentially flow through the first conduit group and the second conduit group.

In one embodiment, in operation, a first part of the working fluid may flow through the first conduit group, and, in parallel, a second part of the working fluid, different from the first part, may flow through the second conduit group.

In one embodiment, the first conduit group and the second conduit group may together constitute interleaved first and second mass transfer conduits that form a working fluid flow volume.

In one embodiment, the first conduit group and the second conduit group may be stacked one on top of the other.

In one embodiment, each of the first conduit group and the second conduit group may constitute a bundle of hollow semipermeable membrane fibers.

In one embodiment, each fiber bundle may be an assembly of one or more layered fiber mats.

In one embodiment, the first conduit group and the second conduit group may form one or more cuboid stacked fiber mats.

In one embodiment, the first conduit group may define a first fluid exchange medium flow direction, and the second conduit group may define a second fluid exchange medium flow direction, and the first flow direction and the second flow direction may be set at an angle of 90° with respect to each other.

In one embodiment, the device may be a cylindrical wound fiber mat device.

In one embodiment, each fiber bundle may have a ring shaped or ring section shaped cross-section, and the fiber bundles may be nested around a common central longitudinal axis.

In one embodiment, the fibers in each fiber bundle may have an open-loop shape.

In one embodiment, the fibers of all the fiber bundles may be looped around a common central longitudinal axis of the working fluid treatment device.

In one embodiment, the integrated working fluid treatment chamber may further include a third conduit group of heat exchange conduits for heat exchange between the working fluid and a heat exchange fluid.

In one embodiment, the device may be adapted to treat blood as the working fluid, wherein the first conduit group may be adapted to oxygenate the blood, and the second conduit group may be adapted to deliver nitric oxide into the blood.

In one embodiment, the device may be adapted to treat blood as the working fluid, wherein the first conduit group may be adapted to oxygenate the blood, and the second conduit group may be adapted to deliver a narcotic agent into the blood.

According to a further aspect of the present disclosure, there is provided a method of treating a patient during cardiopulmonary bypass surgery using a working fluid treatment device as detailed above.

According to a further aspect of the present disclosure, there is provided an extracorporeal blood treatment device for mass and energy transfer between a patient's blood and fluid exchange media, wherein the extracorporeal blood treatment device comprises a housing defining an internal blood flow cavity with a substantially constant cross-section to flow, and the blood flow cavity is configured for blood flow therethrough across substantially an entire volume of the internal blood flow cavity, wherein the housing accommodates:

- a first mass transfer assembly configured to oxygenate the patient's blood via a first gas exchange medium, the first mass transfer assembly comprising an array of gas transfer conduits that transfer oxygen to the patient's blood, wherein the first mass transfer assembly forms a first gas circuit for the first gas exchange medium;
- a heat exchange assembly configured to heat or cool blood with a heat energy transfer medium, the heat exchange assembly comprising an array of heat transfer conduits that carry the heat energy transfer medium; and
- one or more additional mass transfer assemblies that are configured to provide mass transfer between fluid exchange media and the patient's blood, wherein each additional mass transfer assembly comprises an array of mass transfer conduits for mass transfer of one or more substances from or into the patient's blood;

wherein each additional mass transfer assembly forms a separate fluid circuit for a particular fluid exchange medium that is different and independent from the first gas circuit, wherein the arrays of the one or more additional mass transfer assemblies are co-located within the internal blood flow cavity so that blood flowing through the internal blood flow cavity flows substantially homogeneously around all the conduits of the first mass transfer assembly, the heat exchange assembly and the one or more additional mass transfer assemblies, wherein the arrays of the first mass transfer assembly, the heat exchange assembly and the one or more additional mass transfer assemblies are arranged relative to one another within the internal blood flow cavity so that a continuous blood flow path is defined through the internal blood flow cavity along which blood flows and is treated by all the assemblies, wherein the continuous blood flow path has a blood entry surface at one end and a blood exit surface at an opposite end in an overall blood flow direction, and wherein the overall blood flow direction from the blood entry surface along the blood flow path to the blood exit surface follows substantially a straight line.

In one embodiment, each assembly may comprise an individual inlet and an individual outlet connected to the housing for introduction and removal of respective fluid exchange medium into and from the individual assembly, respectively.

In one embodiment, at least one of the additional mass transfer assemblies may be selected from the group consisting of fluid transfer assemblies configured to transfer specific gases into the patient's blood, wherein the specific gases may be selected from the group consisting of volatile anesthetics (e.g., isoflurane or sevoflurane), nitric oxide (NO) and nitric oxide in a mixture with an inert gas.

In one embodiment, at least one of the additional mass transfer assemblies may be selected from the group consisting of fluid transfer assemblies configured to transfer specific liquids into the patient's blood, wherein the specific liquids may be selected from the group consisting of drugs, buffers and pH-controlling agents in the form of acids or bases.

In one embodiment, at least one of the additional mass transfer assemblies may be configured to remove blood compounds or components circulating in the blood from the blood, such as blood electrolyte, blood plasma, antibodies or endotoxins, and/or at least one of the other mass transfer assemblies may be configured for blood filtration and hemodialysis.

In one embodiment, at least one of the additional mass transfer assemblies may be configured to measure the gas partial pressure of gases in the patient's blood.

In one embodiment, the mass transfer conduits and the gas transfer conduits may be hollow fibers, and the mass transfer conduits and the gas transfer conduits may have a microporous structure.

In one embodiment, each assembly inlet may have a distribution header for distributing the respective fluid exchange medium into the conduits of the assembly.

In one embodiment, the hollow fibers may have open ends that may be spaced from each other and fixed to each other by a layer of a potting material.

In one embodiment, the potting material layers may constitute inlet and outlet plates of the assemblies.

In one embodiment, each assembly inlet may have a distribution header for distributing the respective fluid exchange medium into the conduits of the assembly, and the inlet plates may be arranged at a bottom of the distribution headers.

In one embodiment, the hollow fibers may be provided in the form of fiber mats.

In one embodiment, the conduits of two different assemblies may be set at an angle of 90° to one another and stacked in a pile.

In one embodiment, two assemblies may be paired into one chamber of the device, in which the conduits of one assembly may alternate with the conduits of the other assembly in the direction of the blood flow.

In one embodiment, the assemblies may be arranged as co-centric rings.

In one embodiment, the assemblies may be arranged in loops and stacked on each other.

In one embodiment, the device may further comprise a single blood inlet and a single blood outlet mounted on the housing so that the inlet may introduce patient's blood into the internal blood flow cavity of the device, so that blood may pass across each array in a direction substantially perpendicular to the flow direction of the fluid exchange media.

In one embodiment, when disregarding the arrays of the assemblies, the internal blood flow cavity may be void of any internal partitions or constrictions.

In one embodiment, the first mass transfer assembly may further comprise i) a gas inlet arranged in the housing for admitting oxygen rich gas exchange medium into the first mass transfer assembly; and ii) a gas outlet arranged in the housing for discharging oxygen poor gas exchange medium from the first mass transfer assembly; and each additional mass transfer assembly may further comprise i) a dedicated and separate fluid inlet different from the gas inlet and arranged in the housing for admitting fluid exchange medium into the mass transfer assembly; and ii) a dedicated and separate fluid outlet different from the gas outlet and arranged in the housing for discharging fluid exchange medium from the mass transfer assembly.

Definitions of terms used in the present disclosure are provided as follows:

Semipermeable membrane: a membrane that allows certain particles to pass through, while others cannot;

Traversing-pore membrane: a semipermeable membrane traversed by open micropores for increased mass transfer across the membrane. The wall of a traversing-pore membrane has numerous pores extending across the entire wall thickness. The pores are open on both sides of the membrane wall. A traversing-pore membrane is liquid tight. Due to its susceptibility to long-term wetting, a traversing-pore membrane is typically only used in short-term applications such as a CPB. It is generally not suited for long-term use such as an ECMO therapy. Commercially available non-limiting examples of traversing-pore membranes are OXYPHAN™ (a polypropylene capillary membrane produced by Thermally Induced Phase Separation (TIPS) technology) and the Membrana™ Oxygenation Membrane Series (capillary membranes produced by extrusion of polypropylene in which consecutive anneal and stretch steps create pores in the capillary wall of the membrane) sold by the company 3M™. Polypropylene is one material suited for the manufacture of traversing-pore membranes.

Diffusion membrane: a semipermeable membrane comprising a nonporous layer preventing long-term membrane wetting. The nonporous layer may take the form of an outer skin. Gas may transit across the nonporous layer by first dissolving into the layer material on one side of the layer and then leaking out of the layer material on the other side of the layer. A diffusion membrane is liquid tight. It is particularly designed for long-term use such as with an ECMO therapy. A commercially available non-limiting example of a diffusion membrane is OXYPLUS™ (an integral asymmetric hollow fiber oxygenation membrane made from polymethylpentene that is processed using TIPS technology) sold by the company 3M™. Polymethylpentene is one material suited for the manufacture of diffusion membranes.

Heat-exchange fiber: a fluid-tight fiber for temperature-controlling a working fluid such as blood. Unlike a gas-exchange fiber, which is made of a semipermeable membrane, a heat-exchange fiber is made of a fluid-tight material with good heat conduction properties. A commercially available non-limiting example of a heat-exchange fiber is HEXPET™ (a transparent heat-exchange capillary made from polyethyleneterephthalate, which is a polyester) sold by the company 3M™. Polyethyleneterephthalate (PET) is one material suited for the manufacture of heat-exchange fibers.

Homogeneous flow: a laminar flow of fluid with a constant pressure and flow rate throughout the flow;

Working fluid: a gas or liquid used to perform a certain type of function or work. Blood is one type a working fluid since it is a liquid used to transport substances around the human body;

Straight line: a working fluid has an overall flow direction that follows a straight line if the outer bounds of the flow remain straight across the whole relevant section of the flow;

Mass transfer: mass transfer refers to the transfer of a substance having mass, such as gases (e.g., oxygen, carbon dioxide ($CO_2$), nitrous oxide ($N_2O$), volatile anesthetics (e.g., isoflurane or sevoflurane), nitric oxide (NO) and nitric oxide in a mixture with an inert gas, etc.) and/or liquids (e.g., blood plasma, drugs, electrolytes, buffers and pH-controlling agents in the form of acids or bases, etc.), either into or out of the working fluid.

A further aspect of the present disclosure pertains to a cardiopulmonary bypass system such as a heart-lung machine, which includes the blood treatment device of the present disclosure, as well as other components such as a pump, a bubble trap, an arterial filter, a bubble or other sensor, and the like.

BRIEF DESCRIPTION OF THE DRAWINGS

The disclosure will now be described by way of non-limiting example only, with reference to the accompanying drawings, in which.

DETAILED DESCRIPTION OF THE DISCLOSURE

The present disclosure pertains to an integrated device dedicated to mass transfer between a working fluid and at least two different fluid exchange media. This device can be used to remove substances from, or add substances to, a wide range of working fluids in all sorts of chemical engineering applications. A preferred application of embodiments of this disclosure is the medical treatment of human blood; however, application of embodiments of this disclosure extends to fluids other than human blood.

The present disclosure is, in particular, directed to an innovative extracorporeal blood treatment device that, besides adding oxygen to a patient's blood stream and temperature-controlling the same, can at the same time add to or remove from the blood further substances efficiently, effectively and safely, in a minimally invasive manner. In a non-limiting exemplary embodiment, the device is adapted to directly access a patient's vascular system. The extracorporeal blood treatment device is, in accordance with certain non-limiting embodiments, specifically designed to remove from, or add to, a flow of a patient's blood various substances in a single pass. The device may be used for various medical-surgical applications, including cardiopulmonary bypass surgery, the delivery of narcotics, such as Isoflurane or Sevoflurane, the addition of nitric oxide to a patient's blood, or blood pH control, to name just a few medical-surgical applications.

Figure 1:
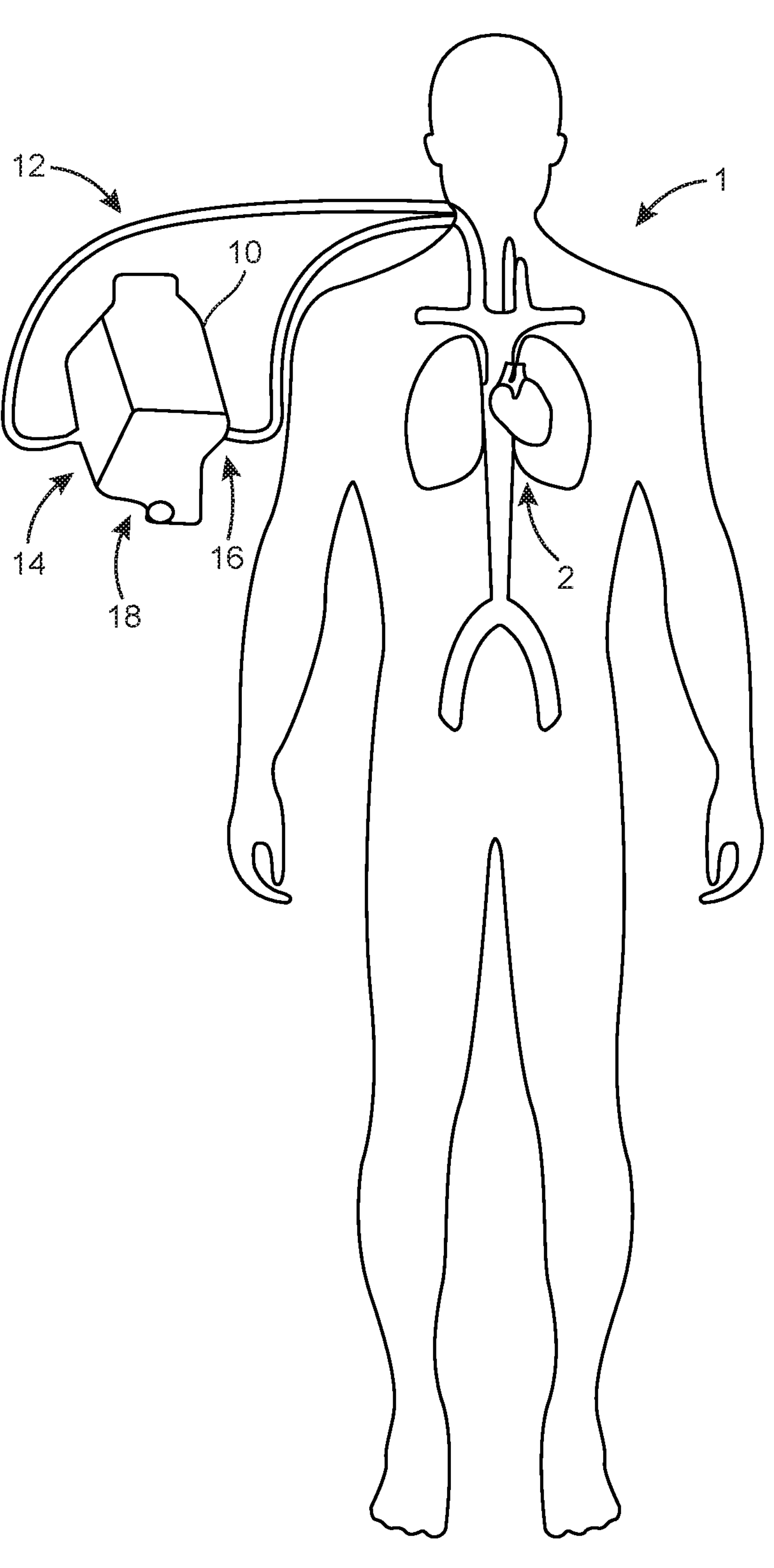
FIG. 1 shows an exemplary blood treatment device attached to a patient's jugular vein using a dual lumen catheter.

FIG. 1 illustrates an exemplary use of the blood treatment device, which is identified by the reference number 10. The blood treatment device 10 is connected to the blood circuit of a patient 1 via tubing 12. As a result, the patient's blood bypasses her lungs 2 and instead circulates across the blood treatment device 10. The blood treatment device 10 effectively acts as artificial lungs, and oxygenates the patient's blood during, e.g., a surgical intervention such as a cardiopulmonary bypass procedure, an ECMO procedure or a PALP procedure.

The blood treatment device 10 has a blood inlet 14 and a blood outlet 16. Both the inlet 14 and the outlet 16 are part of a housing 18 of the blood treatment device 10.

The blood treatment device 10 has an internal blood flow cavity. The internal blood flow cavity sits at the center of the blood treatment device 10. Mass and heat transfer with the blood takes place in the internal blood flow cavity.

Figure 2:
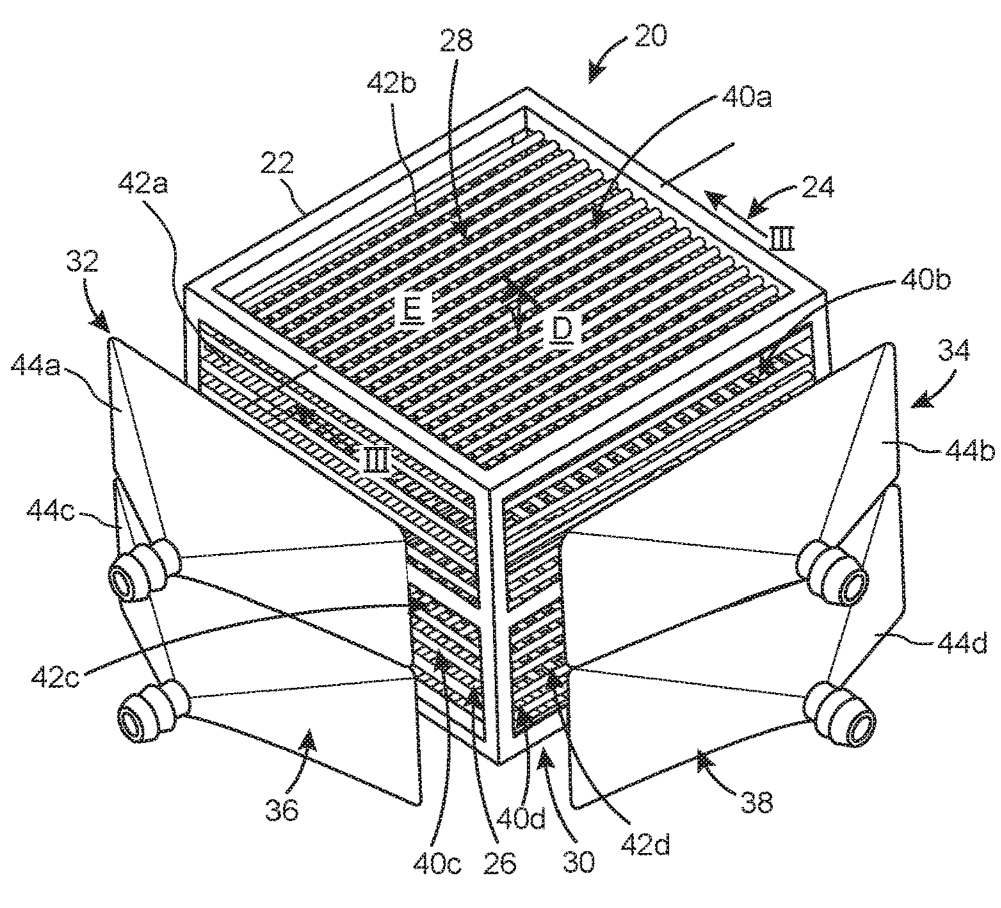
FIG. 2 shows a first non-limiting embodiment of a working fluid treatment device according to the present disclosure.

FIG. 2 shows the internal blood flow cavity 20 of the blood treatment device 10. The internal blood flow cavity 20 is delimited by a box-shaped frame 22. The frame 22 is subdivided into two blood circulation chambers 24 and 26. Blood enters the blood flow cavity 20 from the top 28, transits through the two chambers 24, 26, and exits the blood flow cavity 20 at its bottom 30. In other words, top 28 corresponds to the cavity's blood inlet, and bottom 30 to the cavity's blood outlet. Here, the blood outlet 30 is located opposite to the blood inlet 28. Chamber 24 is a top chamber and chamber 26 is a bottom chamber based on direction of blood flow. Accordingly, the blood flow cavity 20 is configured for blood flow therethrough across substantially its entire volume. In this context, substantially means within 10% of the entire volume. One will note that the cross-section of the internal blood flow cavity 20 is substantially constant. In this context, substantially means a constant cross section with a variation of less than 10%.

In addition to the internal blood flow cavity 20, the blood treatment device 10 includes a first mass transfer assembly 32 configured to oxygenate a patient's blood via a first gas exchange medium. Included as well is a heat exchange assembly 34 configured for temperature-controlling the patient's blood circulating through the blood treatment device 10.

The blood treatment device 10 also has two additional mass transfer assemblies 36 and 38. In the present non-limiting example, the mass transfer assembly 36 is configured to deliver nitric oxide to the patient's blood. It may thus be called a nitrogenator 36. The second additional mass transfer assembly 38 may, for example, be configured for the delivery of volatile anesthetics to the patient's blood. It may thus be called an anesthetics delivery assembly 38.

Figure 3:
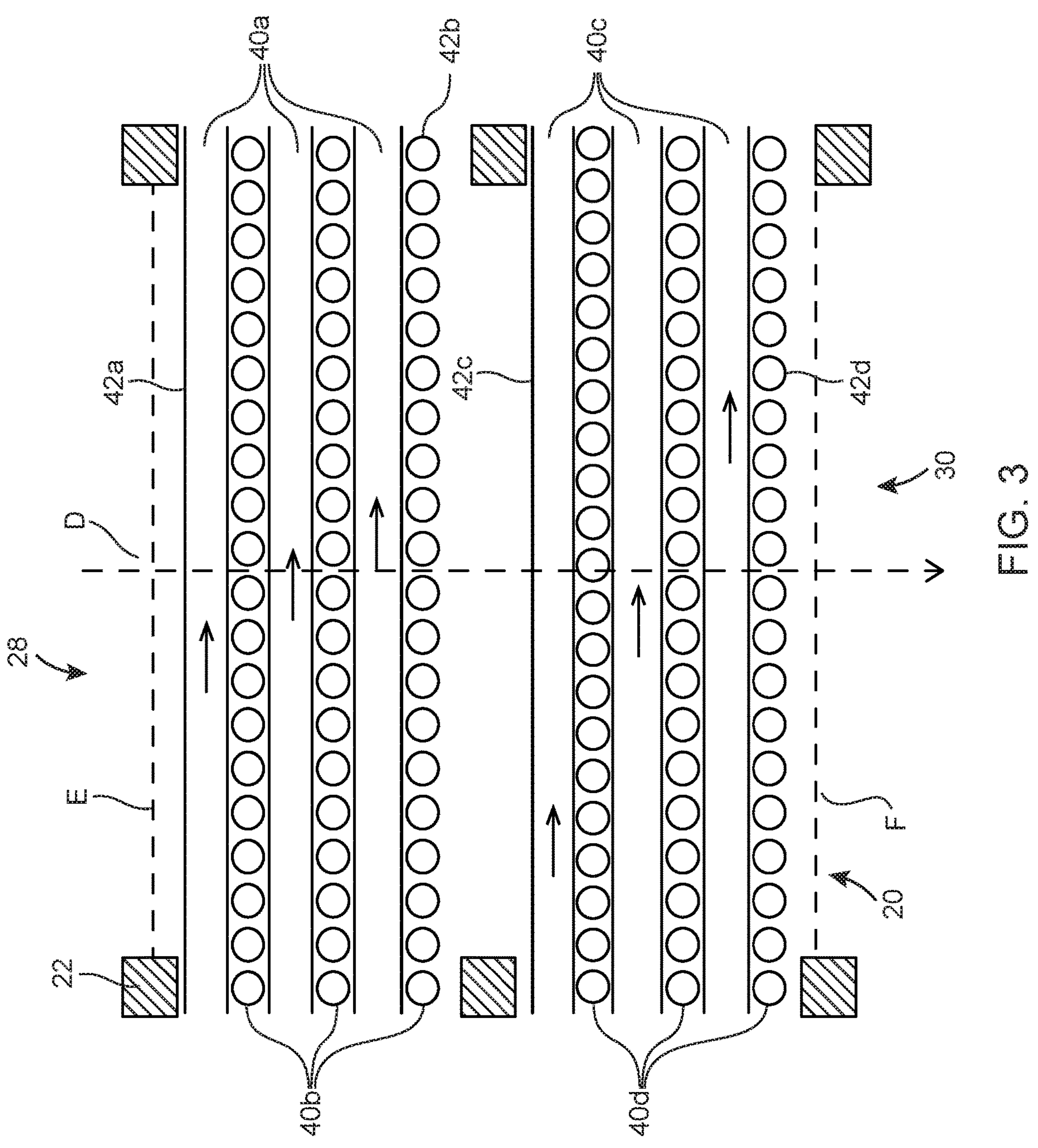
FIG. 3 is a schematic cross-sectional view along the line III-III of FIG. 2.

As shown schematically in FIG. 3, each of the assemblies 32, 34, 36 and 38 comprises an array 40*a* to 40*d* of fluid exchange medium carrying conduits 42*a* to 42*d*. The oxygenator array 40*a* is located in the top chamber 24 of the internal blood flow cavity 20. The heat transfer array 40*b* is also located in the top chamber 24. The nitrogenator array 40*c* is arranged in the cavity's bottom chamber 26. The anesthetics delivery array 40*d* is also arranged in the bottom chamber 26.

All the assemblies 40*a* to 40*d* may be made of a stack of mat layers. In the non-limiting example shown in FIG. 2, each stack consists of three layers or mats. Each individual layer or mat comprises a multitude of individual conduits 42*a* to 42*d*. The conduits 42 within one mat are spaced apart from each other and run parallel to each other as shown in FIGS. 2 and 3.

In the embodiment shown in FIGS. 2 and 3, the three mats of the oxygenator array 40*a* are intermeshed with the three mats of the heat exchanger array 40*b*. Likewise, the three mats of the nitrogenator array 40*c* are intermeshed with three mats of the anesthetics delivery array 40*d*.

The conduits 42*a* to 42*d* of each of the arrays have specific material properties so that they are suited to their dedicated task. For example, all the conduits 42*a* to 42*d* may be hollow fibers, but the transfer conduits 42*a*, 42*c* and 42*d* of the oxygenator, nitrogenator and the anesthetics delivery assembly may have a microporous structure to permit appropriate mass transfer, whereas the hollow fibers 42*b* forming the conduits of the heat exchange assembly must be fluid tight. The heat exchange assembly 34 exchanges energy, not mass, so its fibers 42*b* do not have a microporous structure. In one embodiment, the oxygen exchange conduits 42*a* of the oxygenator and the nitric oxide exchange conduits 42*c* of the nitrogenator may be made of a diffusion membrane to prevent long-term wetting. In one embodiment, the anesthetics delivery conduits 42*d* may be made of a traversing-pore membrane, which is suitably permeable to volatile anesthetics.

In the embodiment shown in FIG. 2, the conduits 42*a* of the oxygenator assembly 32 and the conduits 42*b* of the heat exchanger assembly 34 are set at an angle of 90° to one another.

Likewise, the conduits 42*c* of the nitrogenator 36, and the conduits 42*d* of the anesthetics delivery assembly 38, are set at an angle of 90° to one another.

The conduits of one assembly may also be set at a different angle than 90° to the conduits of another assembly.

The arrays 40*a* to 40*d* of all the assemblies are co-located within the internal blood flow cavity 20. Accordingly, blood flowing through the internal blood flow cavity 20 flows substantially homogeneously around all the assemblies' conduits 42*a* to 42*d*, as a result of symmetry and space efficiency of construction of the various assemblies 32, 34, 36 and 38 with one another.

The arrays 40*a* to 40*d* are arranged relative to one another within the internal blood flow cavity 20 such that they together define a continuous blood flow path through the internal blood flow cavity 20 along which blood can flow, and thus be treated by all the assemblies 32, 34, 36 and 38 during a single pass.

As shown in FIG. 3, the continuous blood flow path has a blood entry surface E at one end and a blood exit surface F at the opposite end. The overall blood flow direction D from the blood entry surface E, along the blood flow path, to the blood exit surface F follows substantially a straight line.

Each of the assemblies 32, 34, 36 and 38 have a dedicated and separate fluid inlet 44*a* to 44*d*, as shown in FIG. 2. Each of these assemblies 32, 34, 36 and 38 also includes a dedicated and separate fluid outlet opposite the fluid inlet, one example 45 of which is shown in FIG. 4. In the shown illustrative example, the inlets and outlets have distribution headers for distributing the respective fluid exchange medium into the assemblies' conduits. Each of the assemblies 32, 34, 36 and 38 forms a separate fluid circuit for its fluid exchange medium, which is different and independent from the fluid circuits of the other assemblies. In other words, each fluid circuit is separate from all the other fluid circuits so there is no intermixing of fluid exchange medium between circuits.

The hollow fibers 42*a* to 42*d* of the assemblies 32, 34, 36, 38, respectively, may be fixed to each other by a layer of potting material. In this case, the potting material layers may constitute inlet and outlet plates of the assemblies. In one variant, the blood flow cavity 20 may be encapsulated by a single integrally formed hollow cuboid potting.

One will note that, in the non-limiting example shown in FIG. 2, the internal blood flow cavity 20 is void of any internal partitions or constrictions, when disregarding the arrays of the assemblies. In other words, other than the arrays 40*a* to 40*d*, which are oriented perpendicularly to the blood flow direction D, there are no internal partitions or constrictions within the blood flow cavity 20. In particular, there are no internal partition or constriction members, which are oriented in the direction D of blood flow.

Operation of the blood treatment device 10 shown in FIGS. 1 to 3 will now be briefly explained. Blood coming from the patient 1 via the tubing 12 enters the blood treatment device 10 at blood entry 14. It is then distributed homogeneously over the entry surface E and, following the general blood flow direction D, transits through the internal blood flow cavity 20. In doing so, it is enriched with oxygen via the oxygenator conduits 42*a*. It is also temperature-controlled via the heat energy transfer medium flowing through the heat exchanger conduits 42*b*. Having been oxygenated and temperature-controlled, the blood leaves the first chamber 24 and reaches the second chamber 26. In the second chamber 26, blood is enriched with nitric oxide via the nitrogenator conduits 40*c*. On top of that, anesthetic gases are diffused into the blood via the anesthetic delivery conduits 40*d*. The oxygenated, temperature-controlled, nitrogenated, and anesthetics carrying blood then leaves the internal blood flow cavity 20 via the lower exit surface F. This complete mass and heat transfer is all achieved with a single pass of blood flowing through the internal blood flow cavity 20.

In an alternative embodiment, the nitrogenator is arranged in the first chamber 24, close to the entry surface E so that nitric oxide is delivered to the blood at the blood inlet of the oxygenator.

The blood treatment device 10 shown in FIGS. 1 to 3 can thus perform four functions essentially simultaneously, namely, providing the patient 1 with the oxygen she needs for her metabolism, maintaining the blood temperature at a physiological level, inhibiting blood platelet activity (adhesion or agglomeration) thanks to the nitric oxide, and anesthetizing the patient 1 for surgery.

In this context, these four functions are construed as essentially simultaneous because they are performed with a single pass of the blood flow. Of course, in accordance with this disclosure, one or more of the assemblies 32, 34, 36 and 38 may be selectively disabled by withholding the flow of fluid exchange medium into its inlet and out of its outlet. For example, during operation of blood treatment device 10, a valve may be used to shut off flow of nitric oxide rich fluid exchange medium to nitrogenator 36 so this assembly is not delivering nitric oxide to the blood flowing through blood flow cavity 20 while the other three assemblies 32, 34 and 38 are operating. In this case, the blood is oxygenated, temperature-controlled and provided with volatile anesthetic(s). In another example, during operation of blood treatment device 10, a separate valve may be used to shut off flow of volatile anesthetic(s) rich fluid exchange medium to the anesthetics delivery assembly 38 so this assembly is not delivering volatile anesthetic(s) to the blood flowing through blood flow cavity 20 while the other three assemblies 32, 34 and 36 are operating. In this case, the blood is oxygenated, temperature-controlled and nitrogenated. Of course, it is possible to operate the blood treatment device 10 so that only assemblies 32 and 34 are in operation so the blood flowing through blood flow cavity 20 is oxygenated and temperature-controlled. In this case, the two valves are used to shut off flow of nitric oxide rich fluid exchange medium to nitrogenator 36 and to shut off flow of volatile anesthetic(s) rich fluid exchange medium to anesthetics delivery assembly 38 at the same time.

Figure 4A:
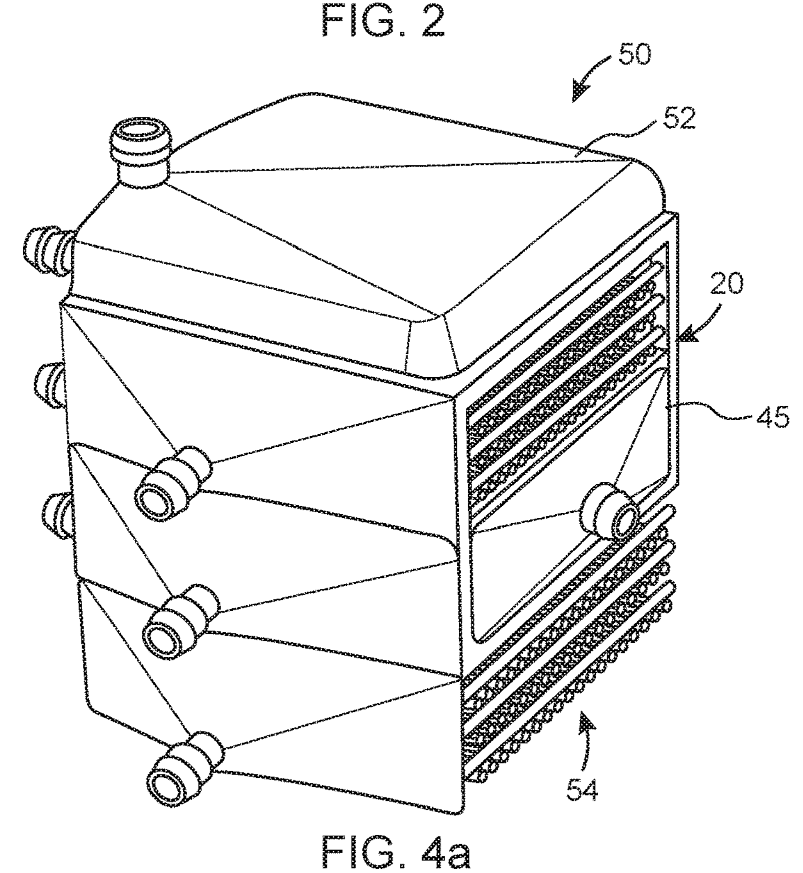
FIGS. 4*a* to 4*e* show a second non-limiting embodiment of a working fluid treatment device according to the present disclosure.
Figure 4B:
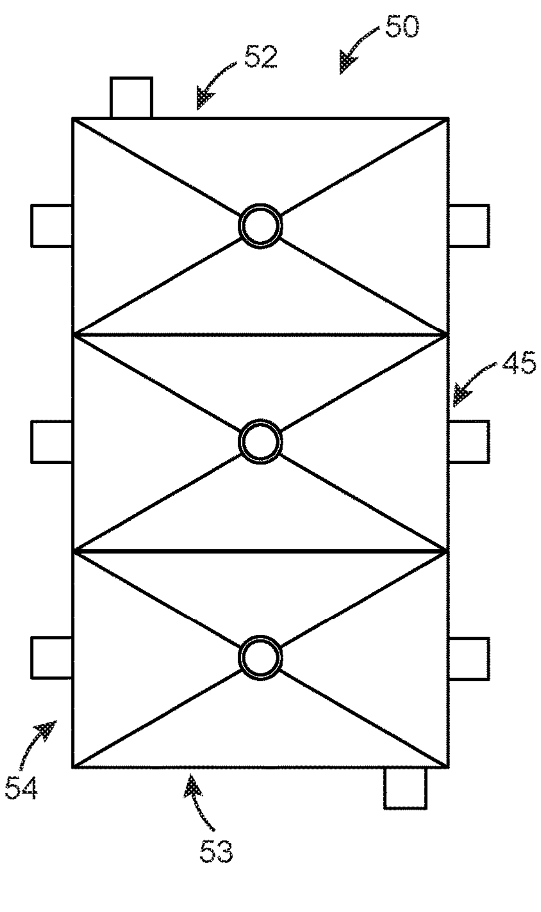
Figure 4C:
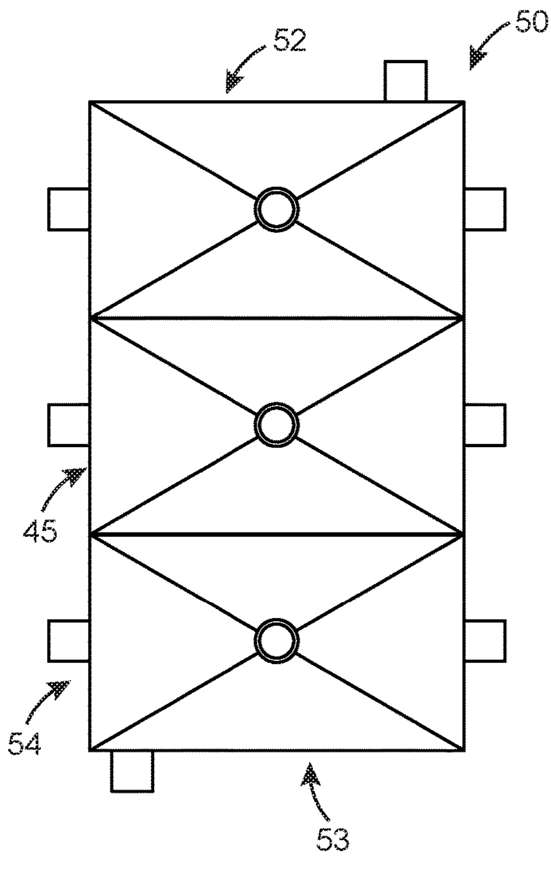
Figure 4D:
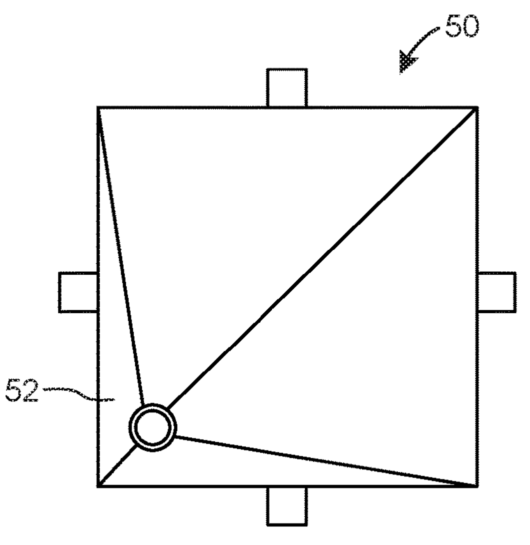
Figure 4E:
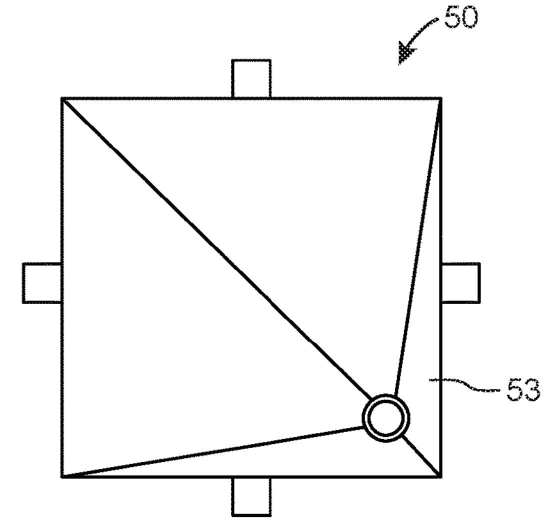

Turning now to FIGS. 4*a* to 4*e*, a second non-limiting embodiment of the blood treatment device of the present disclosure is described. This blood treatment device 50 is in many ways similar to the blood treatment device 10 of FIGS. 1 to 3. In the following, only the differences thereto will be described. FIG. 4*a* is a perspective view of the blood treatment device 50, where some elements have been omitted to provide a view of the device's inner fiber mats. FIGS. 4*b* to 4*e* are a front, back, top and bottom view, respectively of the blood treatment device 50.

The blood treatment device 50 includes a single blood inlet 52 having a distribution header. The inlet 52 is mounted on the housing in such a manner that it introduces the patient's blood into the internal blood flow cavity 20 so that the blood can pass across each array in a direction substantially perpendicular to the flow direction of the fluid exchange media. The blood treatment device 50 also includes a single blood outlet 53.

In contrast to the first embodiment of FIGS. 1 to 3, in this blood treatment device 50, the internal blood flow cavity 20 has three chambers instead of two. Two additional mass transfer assemblies are arranged in the third chamber 54. These additional mass transfer assemblies allow for further blood treatment. For example, one of these additional mass transfer assemblies of the third chamber 54 may provide the patient with a drug while the other one of these additional mass transfer assemblies of the third chamber 54 may provide a buffer or other pH-controlling agent.

Figure 5:
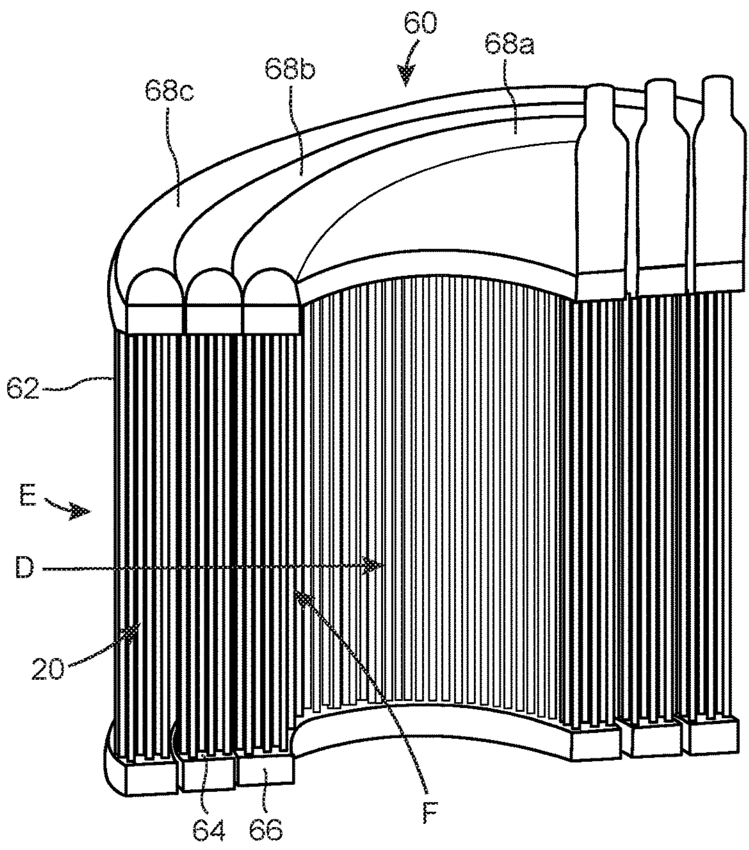
FIG. 5 shows in longitudinal section a third non-limiting embodiment of a working fluid treatment device of the present disclosure.

The principles of the present disclosure are not only applicable to stacked fiber mats blood treatment devices such as the ones shown in FIGS. 1 to 4. These principles may also be applied to wound fiber mat blood treatment devices 60. Such a blood treatment device 60 is shown in FIG. 5. In this variant, there is an outer heat exchanger assembly 62 followed by a middle oxygenator assembly 64, followed by an inner nitrogenator assembly 66. The fluid exchange medium for each of the assemblies 62, 64 and 66 is introduced via a separate header 68*a*, 68*b* and 68*c*, respectively. The three assemblies are ring shaped and arranged concentrically in a cylindrical fashion. The internal blood flow cavity 20 extends from the outer assembly 62 to the inner assembly 66. The internal blood flow cavity thus has a cylindrical ring shape. The blood enters the internal blood flow cavity 20 via the entry surface E located at the outer edge of the outer heat exchanger assembly 62, flows radially through the three assemblies 62, 64 and 66 and exits the internal blood flow cavity 20 via the exit surface F located at the inner edge of the inner nitrogenator assembly 66. While the exit surface F may be slightly less in area than the entry surface F, the working fluid flow cross section remains substantially constant throughout the chamber because the difference in surface area is less than 10%. The general blood flow direction again follows a straight line D. Alternatively, the blood flow may be the opposite way round, meaning that the blood enters the device via the center and then radially flows outwards towards its periphery.

The principles of the present disclosure can also be applied to the third type of extracorporeal blood treatment device, namely to spiral gold/cylindrical fiber loop blood treatment devices. A typical example of such a device is shown in U.S. Pat. No. 5,236,665, the contents of which is incorporated in its entirety into the present disclosure.

Figure 6A:
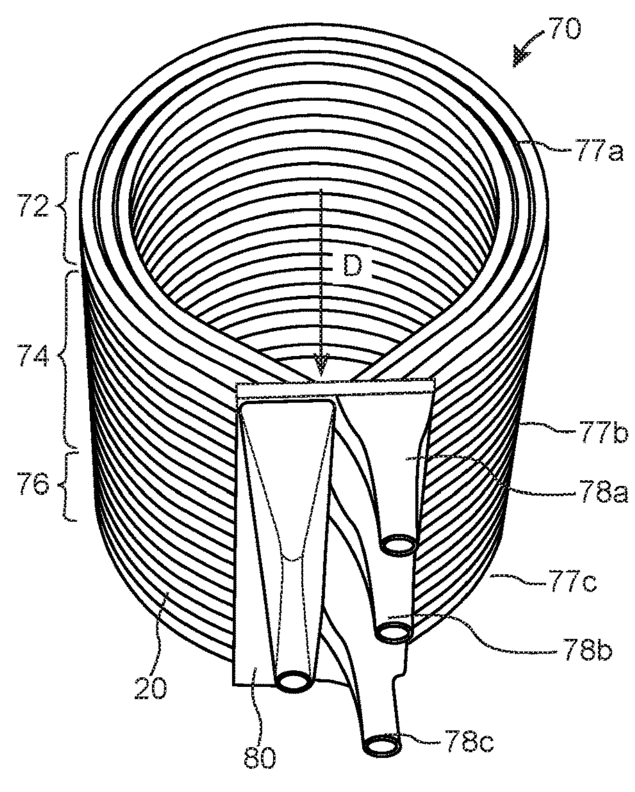
FIGS. 6*a* and 6*b* show a fourth non-limiting embodiment of a working fluid treatment device according to the present disclosure.
Figure 6B:
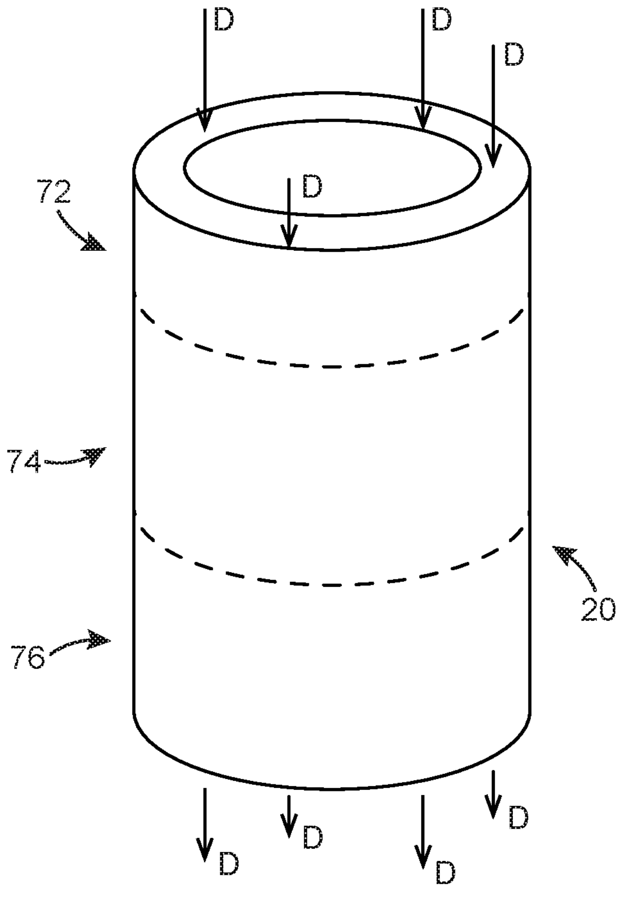

A cylindrical fiber loop blood treatment device 70 according to one exemplary embodiment is illustrated in FIGS. 6*a* and 6*b*. FIG. 6*a* is a view of the stacked spiral fiber arrangement, and FIG. 6*b* is a view of the hollow cylindrical casing that houses the stacked spiral fiber arrangement.

The blood treatment device 70 has three blood treatment assemblies 72, 74 and 76. The three assemblies are stacked on top of each other. Each assembly includes a plurality of fluid exchange medium carrying loops 77*a* to 77*c*. The fluid exchange medium enters its respective assembly 72, 74 and 76 through an inlet 78*a* to 78*c*. The spent fluid exchange medium then leaves its assembly via a header 80, which is common to all three assemblies. For example, assembly 72 may exchange oxygen and serves as an oxygenator, assembly 74 may exchange nitric oxide and serves as a nitrogenator, and assembly 76 may exchange an anesthetic agent and serves as an anesthetics delivery assembly. Of course, one of these assemblies may be used instead to control temperature and serve as a heat exchanger. The internal blood flow cavity 20 corresponds to the volume taken up by the loops of the three assemblies. Blood may flow from the top to the bottom of the stack or the other way round via the sleeve-shaped internal blood flow cavity 20. The blood flow cavity 20 is delimited by the casing shown in FIG. 6*b*. Again, the general blood flow direction D follows a straight line.

Figure 7:
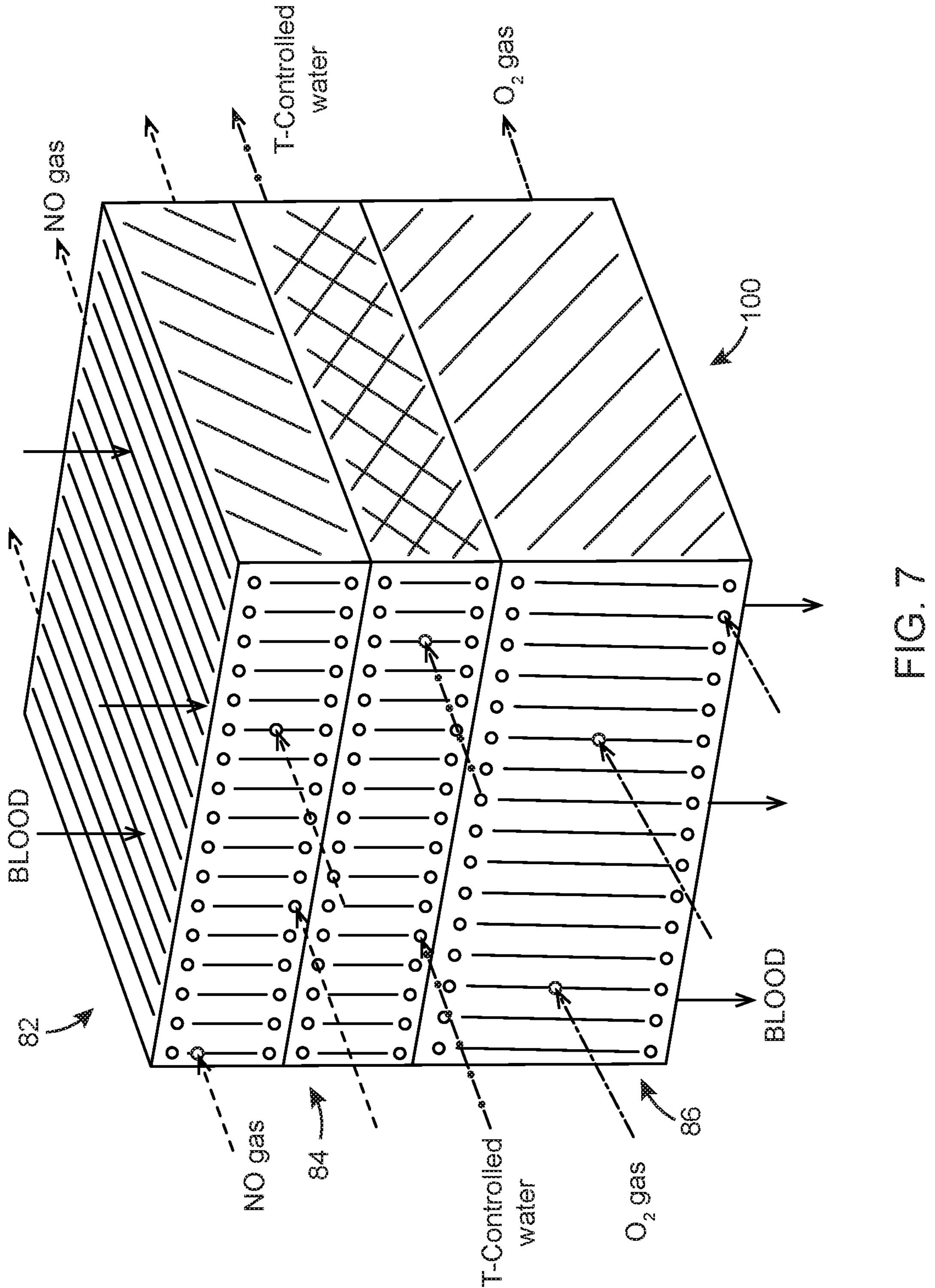
FIG. 7 schematically shows a working fluid treatment device of the present disclosure used for oxygenating, nitrogenating and temperature-controlling human blood.

FIG. 7 is a schematic representation of internal components of yet another blood treatment device 100 of the present disclosure of the cuboid stacked fiber mats design. This device 100 is a combination of a top nitrogenating compartment 82, a middle heat exchanger compartment 84 and a bottom oxygenating compartment 86. Blood flowing through this device first enters the nitrogenating compartment 82, where nitric oxide is added to the blood. Subsequently, the blood traverses the heat exchanger 84, where its thermal temperature is adjusted to a predetermined target value. Finally, the blood crosses the oxygenator 86, where the blood is enriched with oxygen.

Figure 8:
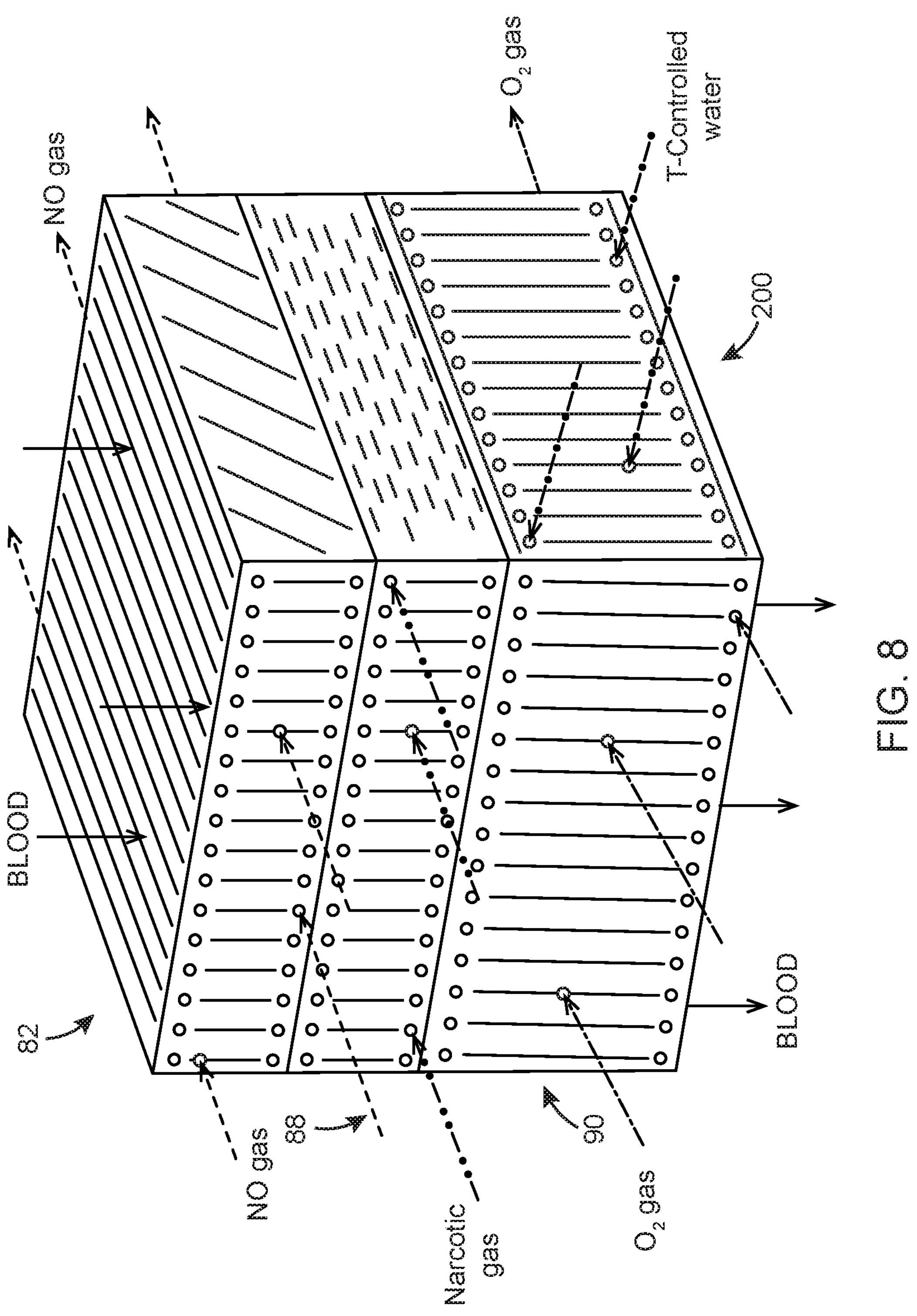
FIG. 8 schematically shows another working fluid treatment device of the present disclosure used for oxygenating, nitrogenating, temperature-controlling and narcotizing human blood.

FIG. 8 is a schematic representation of internal components of yet another blood treatment device 200 of the present disclosure of the cuboid stacked fiber mats design. This device 200 is a combination of a top nitrogenating compartment 82, a middle narcotizing compartment 88 and a bottom integrated heat-exchanging and oxygenating compartment 90. Blood flowing through this device first enters the nitrogenating compartment 82, where nitric oxide is added to the blood. Subsequently, the blood traverses the narcotizer 88, where a narcotic substance, for example sevoflurane, is added to the blood. Finally, the blood crosses the bottom compartment 90, where the blood is enriched with oxygen, and, at the same time, temperature adjusted.

The blood treatment device of the present disclosure may also be put to one or more of the following uses:

A) Mass Exchange Performance Monitoring

A specific test substance/test mass (which is not necessarily needed for the medical application) is added in a certain concentration to a first mass transfer medium flowing through a first mass transfer assembly. The test substance is transferred into the blood stream and subsequently re-diffuses from the blood into another second mass transfer medium flowing through a second mass transfer assembly (downstream, maybe the last mass transfer assembly before the blood outlet). The concentration of the test substance in the second mass transfer medium can then be measured. A higher test substance concentration in the second mass transfer medium indicates a better mass exchange performance of the mass transfer assemblies. This performance test can be done at the beginning of an extracorporeal blood treatment procedure and repeated later on. By comparing the measurement results, one can detect a change in performance during the procedure.

In this way, the mass transfer performance can be monitored without discontinuing or interfering with the extracorporeal blood treatment procedure. A degradation in performance (e.g. because of a clogging or fouling of the mass transfer assemblies) can thus be detected early on. This allows to take corrective measures (such as changing the blood treatment device) to prevent any potential health risks for the patient.

B) Elimination of Antibodies

This can be achieved by attaching specific antigens or biologics to the surface of the mass exchange fibers. For example, the fibers' outer surfaces may be coated with antigens. Antibodies present within the blood flowing through the blood treatment device will then be captured by the immobilized antigens, which leads to antibody removal. In this way, the patient's tissues can be protected from a harmful autoimmune response.

C) Measurement of Gas Pressure within the Blood

Under steady state conditions, there is an equilibrium between the partial and overall gas pressures within the blood on one side of the mass transfer membrane and the partial and overall gas pressures within the gas exchange medium on the other side of the mass transfer membrane. This fact can be used to measure the gas pressures within the blood with the following process: (a) applying a vacuum to the gas exchange fibers until they are fully evacuated, (b) waiting for gas in the blood to diffuse into the fibers' inner lumen via the membranes until there is a pressure equilibrium on both sides of the membranes, and (c) measuring the gas pressures inside the fibers and thus the gas pressures within the blood.

D) Hemofiltration, Plasma Separation and Hemodialysis

The blood treatment device may also include dedicated fibers made of blood filtration membranes. These membranes can be used to remove unwanted elements such as toxic substances from the blood by hemodialysis, or to divide blood into its different constituents by filtration (hemofiltration/hemoconcentration, plasma separation). In this application, the mass transfer through the filtration membrane is driven by a pressure differential (trans-membrane pressure or TMP) across the fiber membrane without impairing hydrostatic pressure of the fluid outside the fiber.

Moreover, embodiments of blood treatment devices described above provide one or more advantages over prior blood treatment devices. One advantage is the usage of different membranes in dedicated segments for different purposes within one device. For example, in case of gases, a microporous membrane of one type may be used for delivery of volatile anesthetics, whereas a diffusive membrane (which is not permeable for volatile anesthetics) is used for the purpose of long-term oxygenation or $CO_2$-removal. Another advantage is the usage of different mass exchange media so that gases and fluids are exchanged within one device in different segments as a result of employing different membranes. This achieves certain practical functionalities such as that of a built-in hemoconcentrator or hemodialyzator. Another advantage is the possibility of absorption of components in the blood (antibodies or toxins (endotoxins)) within a dedicated segment. Another advantage is the possibility of administration of drugs via membranes within a dedicated segment. Another advantage is the possibility of monitoring of the mass exchange performance within the device with dedicated segments. Another advantage is the possibility of measuring of the total gas pressure and the partial gas pressures of the blood within a dedicated segment.

While this disclosure provides multiple exemplary embodiments, it will be understood by those skilled in the art that various changes may be made and equivalents may be substituted for elements thereof without departing from the scope of this disclosure. In addition, many modifications may be made to adapt a particular situation or material to the teachings of this disclosure without departing from the essential scope thereof. Therefore, it is intended that the invention, as defined in the appended claims, not be limited to any particular embodiment disclosed herein, but that the invention will include all embodiments falling within the scope of the claims. Also, in the drawings and the description, there have been disclosed exemplary embodiments and, although specific terms may have been employed, they are unless otherwise stated used in a generic and descriptive sense only and not for purposes of limitation. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item unless otherwise explicitly indicated.

The invention claimed is:

1. A working fluid treatment device for mass transfer between a working fluid and a first fluid exchange medium, and for mass transfer between the same working fluid and a second fluid exchange medium different from the first fluid exchange medium, wherein the working fluid treatment device comprises:

a collective first fluid exchange medium inlet that admits the first fluid exchange medium into the working fluid treatment device;

a collective second fluid exchange medium inlet that is fluidly separate from the first fluid exchange medium inlet, and that admits the second fluid exchange medium into the working fluid treatment device; and an integrated working fluid treatment chamber, wherein the chamber includes a working fluid inlet;

a working fluid outlet;

a first conduit group of first mass transfer conduits disposed between the working fluid inlet and the working fluid outlet, the first conduit group having an entry end that receives the first fluid exchange medium into the first conduit group; and an exit end that discharges spent first fluid exchange medium from the first conduit group, wherein the first conduit group performs mass transfer of a first substance with the working fluid when the first fluid exchange medium flows through the first conduit group; and a second conduit group of second mass transfer conduits disposed between the working fluid inlet and the working fluid outlet, the second conduit group having an entry end that receives the second fluid exchange medium into the second conduit group; and an exit end for discharging spent second fluid exchange medium from the second conduit group, wherein the second conduit group performs mass transfer of a second substance with the working fluid when the second fluid exchange medium flows through the second conduit group;

wherein the first fluid exchange medium inlet is connected to the entry end of the first conduit group in order to collectively convey the first fluid exchange medium into all of the first mass transfer conduits of the first conduit group;

the second fluid exchange medium inlet is connected to the entry end of the second conduit group in order to collectively convey the second fluid exchange medium into all of the second mass transfer conduits of the second conduit group;

the first conduit group and the second conduit group are arranged in the chamber in-between the working fluid inlet and the working fluid outlet so that the working fluid, when travelling from the working fluid inlet into the chamber and then through the chamber and then out of the chamber via the working fluid outlet, flows around the first conduit group of first mass transfer conduits and the second conduit group of second mass transfer conduits;

there is a homogeneous conduit distribution throughout the entire volume of the chamber so that the working fluid flow cross section remains constant throughout the chamber;

the first fluid exchange medium and the first mass transfer conduits of the first conduit group are adapted to oxygenate, decarbonate, or oxygenate and decarbonate the working fluid;

the second fluid exchange medium and the second mass transfer conduits of the second conduit group are adapted to add to or remove from the working fluid one or more further substances other than oxygen, carbon dioxide, or oxygen and carbon dioxide; and the working fluid treatment device is configured to operate with the first fluid exchange medium as a liquid or as a gas, and the working fluid treatment device is configured to operate with the second fluid exchange medium as a liquid or as a gas; and wherein the working fluid comprises blood; and wherein the first fluid exchange medium contains oxygen or is for oxygenation of the blood.

2. The working fluid treatment device of claim 1, wherein the first mass transfer conduits and the second mass transfer conduits are hollow semipermeable membrane fibers.

3. The working fluid treatment device of claim 2, wherein semipermeable membranes making up the semipermeable membrane fibers are liquid impermeable and either traversing-pore membranes traversed by open micropores for increased mass transfer across the membranes or-diffusion membranes comprising a nonporous layer preventing long-term membrane wetting.

4. The working fluid treatment device of claim 3, wherein the semipermeable membranes making up the first mass transfer conduits are traversing-pore membranes, and wherein the semipermeable membranes making up the second mass transfer conduits are diffusion membranes.

5. The working fluid treatment device of claim 4, further comprising a single shared fluid exchange medium outlet connected to the exit ends of the first group and the second conduit group in order to receive the spent first fluid exchange media and the spent second fluid exchange media.

6. The working fluid treatment device of claim 1, further comprising a first fluid exchange medium outlet connected to the exit end of the first conduit group that receives the spent first fluid exchange medium, and a second fluid exchange medium outlet connected to the exit end of the second conduit group that receives the spent second fluid exchange medium, wherein the second fluid exchange medium outlet is fluidly separate from the first fluid exchange medium outlet.

7. The working fluid treatment device of claim 1, wherein the working fluid, when travelling through the device, sequentially flows through the first conduit group and the second conduit group.

8. The working fluid treatment device of claim 1, wherein, in operation, a first part of the working fluid flows through the first conduit group, and, in parallel, a second part of the working fluid, different from the first part, flows through the second conduit group.

9. The working fluid treatment device of claim 1, wherein the first conduit group and the second conduit group together constitute interleaved first mass transfer conduits and second mass transfer conduits that form a working fluid flow volume.

10. The working fluid treatment device of claim 1, wherein the first conduit group and the second conduit group are stacked one on top of the other.

11. The working fluid treatment device of claim 1, wherein each of the first conduit group and the second conduit group constitutes a bundle of hollow semipermeable membrane fibers.

12. The working fluid treatment device of claim 11, wherein each fiber bundle is an assembly of one or more layered fiber mats.

13. The working fluid treatment device of claim 12, wherein the first conduit group and the second conduit group form one or more cuboid stacked fiber mats.

14. The working fluid treatment device of claim 13, wherein the first conduit group defines a first fluid exchange medium flow direction, and the second conduit group defines a second fluid exchange medium flow direction, and wherein the first flow direction and the second flow direction are set at an angle of 90° with respect to each other.

15. The working fluid treatment device of claim 12, wherein the device is a cylindrical wound fiber mat device.

16. The working fluid treatment device of claim 15, wherein each fiber bundle has a ring shaped or ring section shaped cross-section, and the fiber bundles are nested around a common central longitudinal axis.

17. The working fluid treatment device of claim 11, wherein the fibers in each fiber bundle have an open-loop shape.

18. The working fluid treatment device of claim 17, wherein the fibers of all the fiber bundles are looped around a common central longitudinal axis of the working fluid treatment device.

19. The working fluid treatment device of claim 1, wherein the integrated working fluid treatment chamber further includes a third conduit group of heat exchange conduits for heat exchange between the working fluid and a heat exchange fluid.

20. The working fluid treatment device of claim 1, wherein the second conduit group is adapted to deliver nitric oxide or a narcotic agent into the blood.

21. A method of treating a patient during cardiopulmonary bypass surgery using the working fluid treatment device of claim 20.

22. The working fluid treatment device of claim 1, further comprising a single shared fluid exchange medium outlet connected to the exit ends of the first conduit group and the second conduit group in order to receive the spent first fluid exchange media and the spent second fluid exchange media.

23. The working fluid treatment device of claim 2, further comprising a single shared fluid exchange medium outlet connected to the exit ends of the first conduit group and the second conduit group in order to receive the spent first fluid exchange media and the spent second fluid exchange media.

24. The working fluid treatment device of claim 3, further comprising a single shared fluid exchange medium outlet connected to the exit ends of the first conduit group and the second conduit group in order to receive the spent first fluid exchange media and the spent second fluid exchange media.

25. The working fluid treatment device of claim 1, wherein the collective second fluid exchange medium inlet is isolated from the first fluid exchange medium inlet.

26. A working fluid treatment device for mass transfer between a working fluid and a first fluid exchange medium, and for mass transfer between the same working fluid and a second fluid exchange medium different from the first fluid exchange medium, wherein the working fluid treatment device comprises:

a collective first fluid exchange medium inlet that admits the first fluid exchange medium into the working fluid treatment device;

a collective second fluid exchange medium inlet that is fluidly separate from the first fluid exchange medium inlet, and that admits the second fluid exchange medium into the working fluid treatment device; and an integrated working fluid treatment chamber, wherein the chamber includes a working fluid inlet;

a working fluid outlet;

a first conduit group of first mass transfer conduits disposed between the working fluid inlet and the working fluid outlet, the first conduit group having an entry end that receives the first fluid exchange medium into the first conduit group; and an exit end that discharges spent first fluid exchange medium from the first conduit group, wherein the first conduit group performs mass transfer of a first substance with the working fluid when the first fluid exchange medium flows through the first conduit group; and a second conduit group of second mass transfer conduits disposed between the working fluid inlet and the working fluid outlet, the second conduit group having an entry end that receives the second fluid exchange medium into the second conduit group; and an exit end for discharging spent second fluid exchange medium from the second conduit group, wherein the second conduit group performs mass transfer of a second substance with the working fluid when the second fluid exchange medium flows through the second conduit group;

wherein the first fluid exchange medium inlet is connected to the entry end of the first conduit group in order to collectively convey the first fluid exchange medium into all of the first mass transfer conduits of the first conduit group;

the second fluid exchange medium inlet is connected to the entry end of the second conduit group in order to collectively convey the second fluid exchange medium into all of the second mass transfer conduits of the second conduit group;

the first conduit group and the second conduit group are arranged in the chamber in-between the working fluid inlet and the working fluid outlet so that the working fluid, when travelling from the working fluid inlet into the chamber and then through the chamber and then out of the chamber via the working fluid outlet, flows around the first conduit group of first mass transfer conduits and the second conduit group of second mass transfer conduits;

the working fluid being subjected to mass transfer by both the first conduit group and the second conduit group during a single pass of the working fluid through the chamber;

there is a homogeneous conduit distribution throughout the entire volume of the chamber so that the working fluid flow cross section remains constant throughout the chamber;

the first fluid exchange medium and the first mass transfer conduits of the first conduit group are adapted to oxygenate, decarbonate, or oxygenate and decarbonate the working fluid;

the second fluid exchange medium and the second mass transfer conduits of the second conduit group are adapted to add to or remove from the working fluid one or more further substances other than oxygen, carbon dioxide, or oxygen and carbon dioxide; and the working fluid treatment device is configured to operate with the first fluid exchange medium as a liquid or as a gas, and the working fluid treatment device is configured to operate with the second fluid exchange medium as a liquid or as a gas.

27. A working fluid treatment device for mass transfer between a working fluid and a first fluid exchange medium, and for mass transfer between the same working fluid and a second fluid exchange medium different from the first fluid exchange medium, wherein the working fluid treatment device comprises:

a collective first fluid exchange medium inlet that admits the first fluid exchange medium into the working fluid treatment device;

a collective second fluid exchange medium inlet that is fluidly separate from the first fluid exchange medium inlet, and that admits the second fluid exchange medium into the working fluid treatment device; and an integrated working fluid treatment chamber, wherein the chamber includes a working fluid inlet;

a working fluid outlet;

a first conduit group of first mass transfer conduits disposed between the working fluid inlet and the working fluid outlet, the first conduit group having an entry end that receives the first fluid exchange medium into the first conduit group; and an exit end that discharges spent first fluid exchange medium from the first conduit group, wherein the first conduit group performs mass transfer of a first substance with the working fluid when the first fluid exchange medium flows through the first conduit group; and a second conduit group of second mass transfer conduits disposed between the working fluid inlet and the working fluid outlet, the second conduit group having an entry end that receives the second fluid exchange medium into the second conduit group; and an exit end for discharging spent second fluid exchange medium from the second conduit group, wherein the second conduit group performs mass transfer of a second substance with the working fluid when the second fluid exchange medium flows through the second conduit group;

wherein the first fluid exchange medium inlet is connected to the entry end of the first conduit group in order to collectively convey the first fluid exchange medium into all of the first mass transfer conduits of the first conduit group;

the second fluid exchange medium inlet is connected to the entry end of the second conduit group in order to collectively convey the second fluid exchange medium into all of the second mass transfer conduits of the second conduit group;

the first conduit group and the second conduit group are arranged in the chamber in-between the working fluid inlet and the working fluid outlet so that the working fluid, when travelling from the working fluid inlet into the chamber and then through the chamber and then out of the chamber via the working fluid outlet, flows around the first conduit group of first mass transfer conduits and the second conduit group of second mass transfer conduits;

there is a homogeneous conduit distribution throughout the entire volume of the chamber so that the working fluid flow cross section remains constant throughout the chamber;

the first fluid exchange medium and the first mass transfer conduits of the first conduit group are adapted to oxygenate, decarbonate, or oxygenate and decarbonate the working fluid;

the second fluid exchange medium and the second mass transfer conduits of the second conduit group are adapted to add to or remove from the working fluid one or more further substances other than oxygen, carbon dioxide, or oxygen and carbon dioxide;

the working fluid treatment device being configured for extracorporeal blood circulation; and the working fluid treatment device is configured to operate with the first fluid exchange medium as a liquid or as a gas, and the working fluid treatment device is configured to operate with the second fluid exchange medium as a liquid or as a gas.

* * * * *